(12) United States Patent
Maggi et al.

(10) Patent No.: US 10,449,147 B2
(45) Date of Patent: Oct. 22, 2019

(54) PHARMACEUTICAL COMPOSITION CONTAINING BUDESONIDE AND FORMOTEROL

(71) Applicant: Zambon S.P.A., Bresso (MI) (IT)

(72) Inventors: Loretta Maggi, Piacenza (IT);
Giovanni Caponetti, Piacenza (IT);
Marco Sardina, Gerenzano (IT);
Franco Castegini, Vicenza (IT)

(73) Assignee: Zambon S.P.A., Bresso (MI) (IT)

( * ) Notice: Subject to any disclaimer, the term of this patent is extended or adjusted under 35 U.S.C. 154(b) by 0 days.

(21) Appl. No.: 15/517,672

(22) PCT Filed: Oct. 7, 2015

(86) PCT No.: PCT/EP2015/073190
§ 371 (c)(1),
(2) Date: Apr. 7, 2017

(87) PCT Pub. No.: WO2016/055546
PCT Pub. Date: Apr. 14, 2016

(65) Prior Publication Data
US 2017/0326067 A1    Nov. 16, 2017

(30) Foreign Application Priority Data

Oct. 8, 2014  (IT) .............. MI2014A1762

(51) Int. Cl.
| A61K 9/00 | (2006.01) |
| A61K 9/16 | (2006.01) |
| A61K 31/167 | (2006.01) |
| A61K 31/58 | (2006.01) |

(52) U.S. Cl.
CPC .......... *A61K 9/0075* (2013.01); *A61K 9/1617* (2013.01); *A61K 9/1623* (2013.01); *A61K 31/167* (2013.01); *A61K 31/58* (2013.01)

(58) Field of Classification Search
CPC .... A61K 9/0075; A61K 31/167; A61K 31/58; A61K 9/1617; A61K 9/1623
See application file for complete search history.

(56) References Cited

U.S. PATENT DOCUMENTS

2008/0226736 A1 * 9/2008 Caponetti ............ A61K 9/0075
424/489

FOREIGN PATENT DOCUMENTS

| EP | 1 086 697 A2 | 3/2001 | |
| EP | 2 682 098 A2 | 1/2014 | |
| WO | WO-00/33789 A2 | 6/2000 | |
| WO | WO-0051591 A1 * | 9/2000 | .......... A61K 9/0075 |
| WO | WO-03/024396 A2 | 3/2003 | |
| WO | WO-2007/045689 A2 | 4/2007 | |
| WO | WO-2011/093817 A1 | 8/2011 | |
| WO | WO-2013/109220 A1 | 7/2013 | |
| WO | WO2014/167028 A1 | 10/2014 | |

OTHER PUBLICATIONS

Eur Respir J 2003; 21: 74-81.*

* cited by examiner

*Primary Examiner* — Snigdha Maewall
(74) *Attorney, Agent, or Firm* — Polsinelli PC

(57) ABSTRACT

The present invention relates to inhalation formulations of drugs in the form of dry powder for inhalation administration, suitable for the treatment of obstructive diseases of the airways, such as asthma and chronic obstructive pulmonary disease (COPD). In particular, the invention relates to a pharmaceutical composition for inhalation comprising a first powder comprising budesonide or a pharmaceutically acceptable salt thereof, in an amount greater than 5% by weight of said first powder, leucine in an amount from 5 to 70% by weight of said first powder, lactose in an amount from 20 to 90% by weight of said first powder; a second powder comprising formoterol or a pharmaceutically acceptable salt thereof, in an amount greater than 1% by weight of said second powder, leucine in an amount from 5 to 70% by weight of said second powder, lactose in an amount from 20 to 90% by weight of said second powder and a third powder comprising a mixture of a first lactose which has an X50 from 35 to 75 μm, with a second lactose which has an X50 from 1.5 to 10 μm, the content of said first and second lactose in said mixture being respectively from 85% to 96% and from 4% to 15%. Said composition has a fine particle fraction (FPF) greater than 60% and a delivered fraction (DF) greater than 80%.

20 Claims, No Drawings

PHARMACEUTICAL COMPOSITION CONTAINING BUDESONIDE AND FORMOTEROL

CROSS REFERENCE TO RELATED APPLICATIONS

This application is a National Phase filing under 35 U.S.C. § 371 of PCT/EP2015/073190 filed on Oct. 7, 2015; and this application claims priority to Application No. MI2014A001762 filed in Italy on Oct. 8, 2014 under 35 U.S.C. § 119. The entire contents of each application are hereby incorporated by reference.

The present invention relates to inhalation formulations of drugs in dry powder form for inhalation administration and indicated for the treatment of obstructive diseases of the airways, such as asthma and chronic obstructive pulmonary disease (COPD). In particular, for the treatment of asthma these formulations are indicated both for maintenance therapy and on an as-needed basis.

Inhalation therapy with aerosol preparations is used to administer active agents to the respiratory tract, in the mucosal, tracheal and bronchial regions. The term aerosol describes a nebulized liquid preparation consisting of fine particles carried by a gas (usually air) to the site of therapeutic action. When the site of therapeutic action involves the pulmonary alveoli and small bronchi, the drug must be dispersed in the form of droplets or particles with aerodynamic diameters of less than 5.0 µm.

When the target is the pharyngeal region, larger particles are more appropriate. Conditions suitable for these treatments are represented by bronchospasm, poor compliance, mucosal edema, pulmonary infections and the like.

Currently, administration of drugs in the deep lung region is obtained through inhalation devices such as:
- nebulizers, in which the drug is dissolved or dispersed in the form of suspension and carried to the lung as nebulized droplets;
- powder inhalers, capable of delivering the drug present in the inhaler as dry micronized particles;
- pressurized inhalers, through which the drug—again in the form of droplets of solution or suspension—is carried to the deep lung region by an inert gas expanded rapidly in air by a pressurized canister.

In all these cases, technological problems have been encountered in the development of effective products that, in some cases and for some types of patient, still today limit the administration of drugs by inhalation.

From a clinical point of view, an ideal inhalation product should allow different administration methods to be used by the patient, since the inhalers described are generally suitable for different types of patients and administration conditions. In general, nebulizer therapy is prevalently used by elderly or pediatric patients, while therapy with drugs delivered through powder or pressurized inhalers is more suitable for adults or adolescents. However, the use of nebulizers is currently still today considered effective, since the patient inhales the drug under rest conditions and without using forced inhalation, which is instead required for a drug formulated in an inhalation powder.

Instead, in the case of a pressurized inhaler, the product must be taken coordinating inspiration with activation of the device, to prevent the delivered particles from impacting on the bottom of the throat and failing to reach the deep lung.

From a therapeutic point of view, it is therefore limiting for a patient not to be able to take the same drug in different conditions, such as at home, at work, while travelling and in an emergency. In the different situations indicated, a patient might be obliged to use different drugs and/or formulations containing different active agents.

The most important of the formulation problems encountered in the development of inhalation products concerns chemical stability in relation to atmospheric agents, which cause rapid degradation of the inhalation preparation and, consequently, decrease the shelf life of the product containing this preparation.

The stability of a drug formulated for inhalation is particularly important due to the fact that it must be distributed on the whole lung surface including the alveolar region (deep lung) maintaining its physical properties. Added to this is the fact that the number of excipients currently approved for inhalation administration and therefore that are non-toxic for the pulmonary tissue is very limited.

The literature reports examples of dry inhalation powders with high dispersibility in air due to their low density. These powders are usually formulated with a high content of phospholipids, in particular dipalmitoylphosphatidylcholine (DPPC).

A powder of this kind is described in the patent application US2005/0074498 A1, relating to low density particles, with an internally hollow morphology, obtained by spray-drying with the use of surfactants consisting of phospholipids in combination with a blowing agent. The hollow structure is described as resulting from the precise combination of the blowing agent and of the surfactant phospholipid. The document does not describe examples of similar morphology obtained without phospholipids. The use of phospholipids as surfactants determines the principal features of the product obtained and above all its sensitivity and stability in relation to atmospheric agents, which would be particularly influenced in this case by moisture. Moreover, the patent literature (US 2001/0036481 A1) indicates values of the phospholipid glass-rubber transition temperature (Tg) with humidity of 41° C. for DPPC, 55° C. for distearoylphosphatidylcholine (DSPC) and 63° C. for dipalmitoylphosphatidylethanolamine (DPPE), the three phospholipids most compatible with pulmonary administration.

The transition temperature (Tg) is defined as the temperature required to cause a change in the physical state of the lipids, from the ordered gel phase, in which the hydrocarbon chains are lying flat and closely packed, to the disordered liquid-crystalline phase, in which the hydrocarbon chains are randomly oriented and fluid.

These Tg values are all much lower than the characteristic Tg value of amorphous lactose.

It is known that the closer the Tg is to the temperature of the environment in which the preparation is stored, the easier the transition will be. It is also known that in a system in which the main excipient is fluid and loosely packed, the molecular mobility of the components is very high, and consequently has a propensity to cause different chemical reactions and degradation of the active agents.

Therefore, the solution of producing porous particles for inhalation administration with phospholipids does not appear to be supported by reasonable scientific evaluation in relation to the long term stability of the product.

The aforesaid patent application, besides application as inhalation powder, also describes application of these particles in an inhaler device with a propellant gas. This administration would be impossible with a conventional nebulizer by dispersing the particles in water or aqueous solution, both given the incompatibility of the materials with water and due to their tendency to float on the surface of the liquid or to dissolve slowly therein.

The concept of "high porosity" or "low density" has been used in a substantially equivalent manner in the cited patent applications.

In particular, the term density has been used not to refer to the absolute density of the particles, since this, measured with a helium pycnometer, would identify the density of the solid materials that constitute the powder and the particles according to the equation:

$$\rho = P/V (g/cc)$$

but rather to refer to the apparent density (in some documents by others described as "envelope density") of the particle, considering its overall volume.

Given the technical difficulty of measuring this overall volume for each single particle, the cited patent applications have referred to volume (and subsequently to density) parameters of the powder as bulk volume and tapped volume, which provide a somewhat imprecise indication of the density of the particles that constitute a powder.

The patent application CA2536319 describes a pharmaceutical composition obtained by spray drying, with a moisture content of less than 1%. According to what is indicated, this very low moisture content is necessary to ensure the stability of the composition, as a water content of over 1% in the formulation would cause degradation of the pharmacologically active substances, resulting in a loss of efficacy of the composition. To reduce the level of moisture the composition consists of a large amount of mannitol, which however compromises the physical features of the powder considerably, increasing the particle size and decreasing the dose of powder delivered from the mouthpiece (i.e. inhaled dose) of the inhalation device used.

The problem of producing inhalation powders with high dispersibility has been solved through the engineering of particles that contain the drug as dispersed as possible.

Briefly, the technique used is that of producing essentially fine particles (geometric mean diameter less than 4.0 μm) consisting of small amounts of active agent dispersed at molecular level inside an appropriate matrix of excipients capable of guaranteeing, through the spray—drying preparation technique, the formation of a low density coarse particle.

This formulation approach requires the use of high percentages of excipients, but enables small amounts of active agent to be contained in the composition.

For this reason, although these compositions solve the problem of aerodynamic performance, they fail to solve significant questions in terms of chemical stability.

The production of an inhalation powder in which the content % of active agent is high using a spray-drying technique must instead be considered advantageous in terms of chemical stability. Considering the most common active agents of respiratory therapy, in the majority of cases this content % of active agent would be too high to allow the production of an inhalation powder form, given the limited amount of powder that constitutes an individual dose of product.

In fact, this amount of powder is too small to be dosed reproducibly by any industrial device for producing individual doses of inhalation powders.

Consequently, the production of an inhalation powder that is stable both from a chemical and physical point of view must guarantee the following:

the stability of the active agents used;
adequate aerosol performance or adequate pulmonary deposition of the active agents.

From the point of view of chemical stability, an ideal approach is represented by the production of dry powders containing large amounts of active agent in combination with a sugar capable of decreasing molecular mobility in the particles of powder and a hydrophobic excipient capable of limiting interaction with the external environment and absorption of water by the powder.

From the point of view of aerosol performance, the same powder must be characterized by an adequate particle diameter for inhalation administration and by a composition capable of facilitating particle disaggregation at the time of inhalation.

At the same time, convergence of physical composition features of the powder must coincide with the ability to divide the powder evenly both using single-dose inhaler devices (for products in the form of inhalation powder in individual doses) and multi-dose inhalers capable of regularly drawing a relatively large dose from a storage chamber contained therein.

Normally, in order to reproducibly deliver inhalation powders in an individual dose, carriers and inert fillers are used to enable rapid and efficient dilution of the active agent so that it can be easily metered in inhalers.

Lactose has been used as carrier in powder inhalation formulations (dry powder inhalers—DPI) since it was introduced in 1948 in the Aerohaler inhaler by Abbott.

In fact, lactose represents the only approved carrier for powder inhalation formulations and is used to produce homogeneous formulations in combination with micronized active agents facilitating division accuracy even the case of extremely small doses.

Inhalation formulations in powder form are generally produced as mixtures of coarse carrier particles combined with micronized particles of active agents generally with an aerodynamic diameter from 1-5 um.

Carrier particles are used to increase the flow of the particles of drug, thereby improving division accuracy and reducing variability of the dose observed in formulations containing only the active agent. With this formulation approach, it is possible to increase the size of the dose of powder to be handled, which otherwise would not exceed 1 mg total of active agent, facilitating handling and division of the bulk powders during production operations.

With the use of carrier particles, the particles of drug are emitted from the inhaler (single or multi-dose) more readily and therefore also the delivery efficiency of the powder is increased.

The presence of a coarse carrier such as lactose also provides the patient with feedback during the inhalation phase, since it deposits on the taste buds and produces a blandly sweet sensation, confirming that the dose of drug has been taken correctly. Consequently, the lactose carrier represents an important component of the formulation and any changes to it in chemical and physical terms has the potential to change the lung deposition profile of the drug. Therefore, the design of the carrier particles is important in the development of inhalation powder formulations.

During inhalation, the particles of drug adhering to the surface of the carrier particles detach as a result of the energy of the inhaled air flow that overcomes the adhesion forces between drug and carrier. The coarse particles of the carrier impact in the upper airways while the smaller particles of drug move through the lower airways and are deposited in the deep lung.

Insufficient detachment of the drug particles from those of the carrier due to strong interparticle energies must be considered the main cause of inefficient lung deposition of many powder inhalation products. Therefore, an effective inhalation formulation should be produced identifying the correct balance between adhesive and cohesive interparticle forces so as to guarantee sufficient adhesion between micronized drug and coarse lactose carrier to provide a stable formulation (with homogeneous mixtures and without segregation of powders and suitable uniformity of content) as well as guaranteeing efficacious detachment of the drug from the carrier during inhalation.

Consequently, the efficiency of a powder formulation depends greatly on the properties of the carrier and its selection is a key element for the general performance of the inhalation product.

The range of materials that can be proposed for use as carrier in inhalation pharmaceutical products is extremely limited for toxicological reasons. Lactose and other sugars have been studied and used and consequently certain modifications of these materials can guarantee further formulation optimizations.

Various and controversial reports have been published regarding the most suitable sizes for a carrier for inhalation use. Some studies report improvements in the amounts of respirable drug delivered by a powder inhaler obtained through reducing the sizes of the carrier particles. It has been proposed that certain small agglomerates are more sensitive to turbulent motion in the inhaled air flow, causing more efficient deagglomeration. However, the use of a carrier that is too small causes a worsening in the flow properties of the powder, which is also one of the main reasons for incorporating a coarse carrier in the formulation. On the other hand, it has been reported that carrier particles that are too large normally exhibit larger surface discontinuities, than fine crystals. This can have the advantage of offering protection to the particles of active agent, preventing detachment during the mixing step. Therefore, a large particle size of the carrier is not necessarily a negative element from the point of view of drug deposition after inhalation. Thus, formulations with coarse carriers generally exhibit a better dispersion of the drug than similar formulations obtained with carrier particles of small size.

This is due to weaker interparticle forces in the case of particles of larger sizes.

Even if the influence of the shape of the carrier particles on the dispersibility of the drug of a powder inhalation formulation is not well defined, it is known that the attractive forces between drug and carrier particles can depend on the morphology, in fact the most commonly used particles for powder inhalation formulations have irregular morphology.

The use of inhalation preparations is widely described in the literature for use in the treatment of many diseases affecting the respiratory tract. In particular, the administration of drugs for inhalation use is the preferential treatment for asthma and chronic obstructive pulmonary disease (COPD).

Asthma is chronic inflammatory disease of the airways. The main characteristic of asthma consists in episodic obstruction of the airways, with consequent reduction of the expiratory flow. At times structural changes can be associated with this inflammation of the airways. The prevalence of asthma is high and progressively increasing; it is estimated that at world level this varies from 1% to 18% of the population in different countries, with an estimated 300 million people affected. Deaths caused by asthma in the world each year are estimated at 250,000 and mortality does not seem to be proportionally related with prevalence. Even if from the point of view of the patient and of society the cost of controlling asthma seems high, the related cost of non-treatment is even higher. The aim of treatment is to keep the asthma under control, so that lung function is optimized and symptoms, exacerbations and the need for acute medical treatment and hospitalization are reduced to a minimum. When the symptoms of asthma are controlled, recurrences of the symptoms and severe exacerbations are observed only on rare occasions.

Chronic obstructive pulmonary disease (COPD) is characterized by persistent chronic limitation to the air flow and by a wide range of pathological changes of the lungs, together with some significant extrapulmonary effects that can contribute to the severity of the disease in individual patients. Limitation of the air flow in COPD is not completely reversible and is associated with an abnormal inflammatory response of the lung to inhaled pollutants such as noxious particles or gases. COPD is generally a progressive disease, above all if the patient's exposure to noxious agents is prolonged over time.

COPD is one of the main causes of morbidity and mortality in the world and translates into a substantial and increasing economic and social burden.

The prevalence of COPD is considerably higher in smokers and former smokers than non-smokers, in those over 40 years old than in those under 40 and in men than in women.

The estimation of prevalence of COPD is 15 million patients aged over 40 in the USA.

The estimations of prevalence of COPD in European countries ranges from 1.5 million people with COPD in Spain to 3 million in the United Kingdom, with estimates of 2.7 million people with COPD in Germany, 2.6 million people in Italy and 2.6 million people in France.

Estimates on COPD, which was ranked in sixth place in diseases that cause death in 1990, indicate that it will become the third cause of death in the world within 2020. This increase in mortality is linked to the epidemic expansion of smoking, to pollutants and to demographic changes in the majority of countries, with populations living longer.

The main pharmacological approach in asthma and COPD is based on the use of inhaled (ICS) or systemic corticosteroids (CS) in monotherapy or in association with bronchodilators (long-acting beta agonists: LABA), long-acting muscarin antagonists (LAMA), xanthine and others.

The use of LABAs as monotherapy in asthma patients has proved to increase the risk of adverse events related to asthma including death; therefore, their use is not advisable in monotherapy. The risk of adverse events is less frequent with the combination of inhaled corticosteroids (ICS) and LABAs. Therefore, the use of ICS in combination with LABA will continue to represent a treatment standard in diseases of the airways.

Clinical advantages achieved with combination therapy may be based on molecular interactions between glucocorticoids and β2-adrenoreceptors. Glucocorticoids can increase the number of β2-adrenoreceptors, while β2-agonists can cause nuclear translocation of the glucocorticoid receptors (GR) and their activation.

In the case of persistent asthma, international guidelines recommend the use of inhaled corticosteroids (ICS) at the lowest dosage to guarantee control of the symptoms, optionally combined with a long-acting β2-agonist when the asthma symptoms are not controlled by ICS alone. The addition of LABA therapy to ICS increases the efficacy of the integrated effects in moderate and severe asthma.

It is consolidated information that, in symptomatic adults and in monotherapies with low or also with high doses of ICS, the addition of an LABA to the ICS reduces the frequency of the exacerbations that require the administration of oral steroids, improves symptoms and lung function. Moreover, it also reduces the need to use short-acting β2-agonists as emergency therapy.

In the case of COPD, current international guidelines report that no existing drug has proved capable of modifying the long-term decline in lung function, which is the distinguishing feature of this disease. Pharmacological therapy for COPD is therefore used to reduce symptoms or complications.

Bronchodilators are key to managing the symptoms of COPD, administered on an as-needed or regular basis to prevent or reduce symptoms and exacerbations.

The addition of a regular treatment with ICS to bronchodilators is appropriate for patients with symptomatic COPD with FEV1<50% predicted (stage III: severe COPD and stage IV: very severe COPD) and repeated exacerbations.

Although the use of combined ICS/LABA (in DPI or pMDI formulations) is well consolidated in clinical practice and the collateral effects of ICS are less frequent and less severe than those of steroids administered orally, some considerations on their safety would be advisable, above all as any further research in this field would have to attempt to solve a part of these.

The main safety problems related to the use of inhaled corticosteroids will be explained below.

The global therapeutic effect of ICS depends on their deposition in the airways. However, the majority of the dose delivered, and this depends both on the inhaler used and the inhalation technique, is deposited in the upper airways (mouth, larynx and pharynx) and enters the gastrointestinal tract.

Both absorption routes (gastrointestinal and pulmonary) contribute to the systemic bioavailability, responsible for potential systemic side effects. The dose deposited in the lower airways is absorbed directly into the systemic circulation and the part absorbed by the gastrointestinal tract undergoes first pass hepatic metabolism.

Effects in the oropharynx and the esophagus.

A significant fraction (up to 90%) of the dose delivered can be deposited in the mouth and in the pharynx. This generates the possibility of local adverse effects such as: oral and esophageal candida, dysphonia and cough. To limit the local adverse effects of ICS, it would be useful to reduce the amount of ICS deposited in the oropharynx.

Suppression of the hypothalamic-pituitary-adrenal (HPA) axis.

Long term systemic exposure to exogenous glucocorticoids suppresses the production of endogenous glucocorticoids, so that sudden withdrawal of the exogenous agent can result in acute adrenal insufficiency and adrenal crisis.

Effects on the skin and ecchymosis.

The use of ICS is associated with reduced skin collagen synthesis. High doses of ICS leads to a decrease of skin thickness and ecchymoses, combined with slow healing of skin cuts and sores.

Effects on growth and bone mineral density.

Even if the effects of ICS are controversial, it is known that corticosteroids tend to influence bone mineral density, in particular of the spine.

Other important problems linked to the use of ICS are the potential pharmacological interactions that can occur with other active agents.

All ICS currently available are subject to substantial metabolic conversion in the liver mainly due to the enzymes of the CYP3A4 family. In this sense, in clinical practice, reduced doses of ICS should be used in co-administration with CYP3A4 inhibitors.

The role of ICS on cataracts and glaucoma and their potential effects on insulin resistance are still controversial.

Moreover, even if the side effects of ICS are less frequent and less severe than those of oral steroids, there are still concerns regarding their safety.

For example, around 5-10% of all asthma patients do not respond adequately even to oral steroids.

With regard to COPD, treatment with ICS increases the probability of pneumonia and does not reduce overall mortality. The dose-response ratio and long term safety of ICS in COPD are not known. Only moderate or high doses have been used in long term clinical studies.

The US Food and Drug Administration (FDA) recently issued restrictive recommendations on the use of LABA in the treatment of asthma.

For these reasons, the development of a new formulation that limits the systemic load of both ICS and LABA appears justified and aimed at covering areas of therapeutic need.

As indicated above, the main pharmacological approach for the cure and treatment of asthma and of COPD is currently based on the use of inhaled corticosteroids (ICS) in association with long-acting beta-agonist bronchodilators (LABA). In particular, the association between Budesonide and Formoterol Fumarate formulated in three different doses constitutes the pharmacological reference currently present on the market.

Budesonide is an anti-inflammatory corticosteroid that exhibits a strong glucocorticoid activity and a weak mineralcorticoid activity. Its absorption in the tissues of the airways does not seem to be influenced by lung function with comparable plasma concentrations reached after administration in the lungs of healthy and asthmatic subjects. Once absorbed at intracellular level, Budesonide undergoes reversible conjugation with intracellular fatty acids, that extend its retention within the airways and its range of action. Formoterol fumarate is a long-acting selective beta-2-adrenergic receptor agonist (LABA) with rapid onset of action.

Its solubility in water and moderate lipophilia guarantee rapid diffusion towards the β2-adrenoreceptors on the smooth muscle cells of the airways with a rapid bronchodilating effect.

The patent EP0613371 describes a solid formulation for inhalation use comprising budesonide and formoterol. The formulation is obtained by micronization of the active agents, which are subsequently suspended or dissolved in a suitable propellant liquid. However, this solution has some technological limitations, due both to the nature of the active agents in micronized solid form, and to the method of administration using pressurized inhalers. In fact, when the active agents are micronized and dispersed in a propellant in solid state, they are unable to reach the deepest parts of the lungs. In fact, during storage of the product, they tend to become compacted and agglomerate, forming agglomerates of particles of sizes unsuitable for administration in the lungs. For this reason, in this type of formulation the two active agents are contained in a large amount, in order to compensate for the small amount of drug deposited in the site of action (due to the agglomerates of particles of inappropriate sizes). In this way, the amounts of active agents deposited outside the lung increase, with a consequent potential increase in the side-effects typical of corticosteroids and of β2-agonists. Moreover, in these formulations the doses of powder and active agent delivered by the inhaler are sometimes scarcely reproducible, as the agglomerates of particles that develop during administration compromise delivery of the powder.

In the light of all of the aforesaid considerations, it would be advantageous to be able to produce a pharmaceutical composition for inhalation use for the treatment of asthma and of chronic obstructive pulmonary disease (COPD) in the form of dry powder that is stable and easy to administer with common devices for inhalation powders, while remaining easy to produce.

At the state of the art, the problem of providing an inhalable formulation containing drugs for the treatment of asthma and COPD that enables a satisfactory pharmacological response to be obtained while markedly reducing the quantities of ICS and LABA contained in the formulation remains wholly or partially unsolved. This could potentially reduce the problems described above.

Moreover, it would be useful to have an inhalable powder for the treatment of asthma and COPD that: enables reproducible doses both of ICS and LABA to be obtained when it is
administered using common powder inhalers,
is easy for all patients to inhale, including those with inspiratory difficulties due to respiratory muscle weakness. In fact, these patients would be unable to use a powder inhaler with high resistance and therefore the efficacy of the drugs would be compromised.

A first aspect of the present invention is therefore to provide a pharmaceutical composition for inhalation use comprising:
a) a first powder comprising budesonide or a pharmaceutically acceptable salt thereof, in an amount greater than 5% by weight of the first powder, leucine in an amount from 5 to 70% by weight of the first powder, lactose in an amount from 20 to 90% by weight of the first powder;
b) a second powder comprising formoterol or a pharmaceutically acceptable salt thereof, in an amount greater than 1% by weight of the second powder, leucine in an amount from 5 to 70% by weight of the second powder, lactose in an amount from 20 to 90% by weight of the second powder;
c) a third powder comprising a mixture of a first lactose which has an X50 from 35 to 75 µm, with a second lactose which has an X50 from 1.5 to 10 µm, the content of said first lactose and second lactose in said mixture being respectively from 85% to 96% and from 4% to 15%;
the ratio by weight between the sum of the first and second powder and of the mixture of a first and second lactose is from 1/5 to 1/100.

The composition has a fine particle fraction (FPF) greater than 60% and a delivered fraction (DF) greater than 80%.

A further aspect of the invention is represented by a Kit for administration of a drug as inhalation powder, comprising a metered amount of the composition according to the present invention and an inhalation device.

In particular, the budesonide in the first powder of the composition according to the present invention is present in an amount greater than 7% by weight of the powder in which it is contained.

The formoterol in the second powder of the composition according to the present invention is present in an amount greater than 2% by weight of the powder in which it is contained.

With regard to the molar ratios between the two active agents of the composition of the present invention, the weighted ratio between budesonide and formoterol is preferably from 5:1 to 120:1 preferably from 8:1 to 71:1 and even more preferably from 17:1 to 36:1.

Analyzing the composition in terms of amounts in the formulation as described above, budesonide is present in an amount from 30 to 200 µg while formoterol is present in an amount from 1.5 to 6 µg per inhaled unit dose. Inhaled unit dose is intended as the dose delivered from the mouthpiece of the inhaler with each single inhalation.

In particular, in a first preferred embodiment of the inhalation composition, budesonide is present in an amount from 30 to 50 µg is and formoterol is present in an amount from 1.5 to 3 per inhaled unit dose.

In a second preferred embodiment budesonide is present in an amount from 60 to 100 µg and formoterol is present in an amount from 1.5 to 3 µg per inhaled unit dose.

In a third preferred embodiment budesonide is present in an amount from 140 to 200 µg and formoterol in an amount from 3 to 6 µg per inhaled unit dose.

According to the present invention the powders contained in the pharmaceutical composition of the present description include a hydrophobic substance to reduce moisture sensitivity. This hydrophobic substance is leucine, which also facilitates particle disaggregation. Leucine is present in an amount from 5 to 70% by weight of each powder. Preferably the amount of leucine present in the powders contained in the pharmaceutical composition is from 18 to 55% by weight of each powder.

According to the present invention the first and the second powder contained in the pharmaceutical composition of the present description also contain a sugar, preferably lactose, a disaccharide sugar, in an amount from 20 to 90%, preferably in an amount from 40 to 80% by weight of each powder.

According to the present invention the first and the second powder that constitute the composition comprise a surfactant in an amount from 0.2 to 2% by weight of each powder, preferably in an amount from 0.4 to 0.8% by weight of each powder.

The surfactant of the composition according to the invention can be selected from the various classes of surfactants for pharmaceutical use.

Surfactants considered suitable to be used in the present invention are all those substances characterized by medium or low molecular weight containing a hydrophobic moiety, generally readily soluble in an organic solvent but weakly soluble or totally insoluble in water, and a hydrophilic (or polar) moiety, weakly soluble or completely insoluble in an organic solvent but readily soluble in water. Surfactants are classified according to their polar moiety. Therefore, surfactants with a negatively charged polar moiety are called anionic surfactants, while cationic surfactants contain a positively charged polar moiety. Uncharged surfactants are generally called non ionic, while surfactants with both a positive and negative charge are called zwitterionic. Examples of anionic surfactants are represented by the salts of fatty acids (better known as soaps), sulfates, sulfate ethers and phosphate esters. Cationic surfactants are frequently based on polar groups containing amino groups. The most common non ionic surfactants are based on polar groups containing oligo-(ethylene-oxide) groups. Zwitterionic surfactants are generally characterized by a polar group consisting of a quaternary amine and a sulfuric or carboxylic group.

Specific examples of this application are represented by the following surfactants: benzalkonium chloride, cetrimide, docusate sodium, glyceryl monooleate, sorbitan esters, sodium lauryl sulfate, polysorbates, phospholipids, biliary salts.

Non ionic surfactants, such as polysorbates and polyoxyethylene and polyoxypropylene block copolymers, known as "Poloxamers", are preferred. Polysorbates are described in the CTFA International Cosmetic Ingredient Dictionary as mixtures of sorbitol and sorbitol anhydride fatty acid esters condensed with ethylene oxide. Particularly preferred are non ionic surfactants of the series known as "Tween", in particular the surfactant known as "Tween 80", a polyoxyethylene sorbitan monooleate available on the market.

The presence of a surfactant, and preferably of Tween 80, is necessary to reduce the electrostatic charges found in formulations without it, flow of the powder and maintenance of the homogeneous solid state without initial crystallization.

According to the present invention the third powder comprised in the pharmaceutical composition for inhalation use comprises a mixture of two types of lactose with different particle size. With this powder it is possible to obtain a composition that can be easily divided in the means used for administration, such as the capsules used in inhalation systems, and at the same time obtain a composition with properties of high respirability so that the active agent or agents used can be deposited in deep lung regions and perform their pharmacological action. According to what is described above, a composition comprising a mixture of lactoses that is too fine or too coarse is not an ideal solution for obtaining the respirability results desired. Therefore, the possibility of adding an amount of fine particles of lactose to formulations of inhalation powders already containing coarse lactose powders in order to improve the inhalation efficiency of drugs was evaluated.

Studies conducted confirmed that the presence of fine lactose well associated with coarser lactose is capable of performing a key role in the drug dispersion process. The addition of around 10% of fine lactose in mixtures of active agents and coarse lactose showed that the fine component helps the active agent to detach from the coarse particles. It was also reported that the concentration of fine lactose added must be carefully controlled since the desired dispersibility of the drug can be reached without substantially influencing the flow properties of the drug. On the contrary, the presence of an excess of fine lactose tends to inhibit flow of the powder since this can enter the voids between the larger particles and promote compacting and consequent thickening of the powder. It was also reported that the presence of an excess of fine lactose causes a decrease of the respirable fraction of an inhalation powder.

According to the present invention, the mixture comprises a lactose with larger particle size, i.e. with an X50 (at least 50% of the particles) from 35 to 75 µm present in an amount greater than a second lactose with smaller particle size, i.e. with an X50 from 1.5 to 10 µm. In particular, the lactose with larger particle size is present in the mixture in a percentage by weight of the mixture, from 85 to 96%, while the lactose with smaller particle size is present in the mixture in a percentage by weight of the mixture from 4 to 15%.

According to the present invention, in order to obtain a composition having properties of high respirability, the ratio between the sum of the first and of the second powder containing budesonide and formoterol, and the third powder comprising the mixture of lactoses, is from 1/100 to 1/5. This ratio is dictated by the fact that if the sum of the first and second powder drops below 1/100, performance of the pharmaceutical composition in terms of respirability is not adequate and therefore does not meet the desired properties.

According to the present invention, the term "inhalable" is intended as a powder suitable for pulmonary administration. An inhalable powder can be dispersed and inhaled by means of an appropriate inhaler, so that the particle can enter the lungs and alveoli to provide the pharmacological properties of the active agent of which it is formed. A particle with aerodynamic diameter of less than 5.0 µm is normally considered inhalable.

The term "amorphous" according to the present invention is intended as a powder that contains less than 70% of crystalline fraction, more preferably less than 55%. The pharmaceutical composition described in this text has a ratio between the amount of powder in amorphous form that constitutes the composition expressed by weight and the amount of sugar present in the composition expressed by weight from 0.8 to 2.0. This ratio indicates that the sugar present in the powder is a substantially amorphous sugar, which therefore has a crystalline fraction of less than 50%. This enables the sugar to coordinate the water present in the composition, preventing it from being available to hydrolyze the active agent, thereby making it ineffective.

The term "fine particle fraction (FPF)" is intended as the fraction of powder, with respect to the total delivered by an inhaler, which has an aerodynamic diameter (dae) of less than 5.0 µm. The characterization test that is performed to evaluate this property of the powder is the Multi Stage Liquid Impinger (MSLI) test, as described in the European Pharmacopoeia current ed. The conditions for performing this test consist in subjecting the powder to an inhalation through the inhaler such as to produce a pressure drop of 4 KPa in the system.

The term "delivered fraction (DF)" is intended as the percentage of active agent, with respect to the total loaded, delivered by a powder inhaler in standard inhalation conditions.

The characterization test performed to evaluate this property of the powder is the DUSA test, as described in the European Pharmacopoeia current ed. The conditions for performing this test consist in subjecting the powder to an inhalation through the inhaler such as to produce a pressure drop of 4 KPa in the system. The preferred production process of the powder according to the invention is spray drying starting from a solution of leucine, of a sugar and of a surfactant in which the drug, if present, is dissolved or dispersed as suspension or emulsion.

The preferred particle size for this powder provides that at least 50% of the size distribution (X50) is below 5 preferably below 3 more preferably below 2.0 µm, also to increase the surface area optimizing deep lung deposition.

According to the present invention, the powder that constitutes the pharmaceutical composition is a substantially dry powder, i.e. a powder with a moisture content of less than 10%, preferably less than 5%, more preferably below 3%. This dry powder preferably has no water capable of hydrolyzing the active agent making it inactive. The amount of moisture present in the composition is controlled:

by the presence of leucine which limits its content due to its hydrophobic properties, both during production of the powder and during the subsequent handling steps, and by the sugar that, by trapping the moisture in a structure that becomes increasingly rigid over time, prevents the water from being available to hydrolyze the active agent.

The process for preparing the pharmaceutical composition according to the invention substantially comprises the operations of:

a) providing a first powder obtained by spray drying comprising budesonide or a pharmaceutically acceptable salt thereof, in an amount greater than 5% by weight of the powder, leucine in an amount from 5 to 70% by weight of the powder, substantially amorphous lactose after obtaining the powder by spray drying in an amount from 20 to 85% by weight of the powder;

b) providing at least a second powder obtained by spray drying comprising formoterol or a pharmaceutically acceptable salt thereof, in an amount greater than 1% by weight of the powder, leucine in an amount from 5 to 70% by weight of the powder, substantially amorphous lactose after obtaining the powder by spray drying in an amount from 20 to 85% by weight of the powder;

c) providing a third powder obtained by mixing a first lactose which has an X50 from 35 to 75 µm, with a second lactose which has an X50 from 1.5 to 10 µm, wherein the content of the first lactose and second lactose in the mixture is respectively from 85% to 96% and from 4% to 15%;

d) mixing the powders.

In particular the production process of the composition, in step a) and b) of obtaining the powders by spray drying, consists of a series of operations illustrated below.

These operations are:
preparing a first phase (A) in which an active agent is present in an appropriate liquid medium;
preparing a second phase (B) in which the leucine, the lactose and the surfactants are dissolved or dispersed in an aqueous medium;
mixing said phases (A) and (B) to obtain a third phase (C) in which the liquid medium is homogeneous;
drying said phase (C) in controlled conditions to obtain a dry powder with particles having a size distribution with median diameter of less than 10.0 µm;
collecting said dry powder.

Phase (A) can be either a suspension of the active agent in an aqueous or non aqueous medium or a solution of the active agent in an appropriate solvent.

Preparation of a solution is preferable, and the organic solvent is selected from those soluble in water. In this case, phase (C) is also a solution of all the components of the desired composition.

Instead, when phase (A) is a suspension of the hydrophobic active agent in an aqueous medium, phase (C) is also a suspension in an aqueous medium, which will contain the dissolved soluble components such as the excipients and surfactants.

The drying operation consists of eliminating the liquid medium, solvent or dispersant, from phase (C), to obtain a dry powder with the desired dimensional features. This drying is preferably obtained by spray-drying. The features of the nozzle and the process parameters are selected so that the liquid medium is evaporated from the solution or suspension (C) and a powder with the desired particle size is formed.

The production process of the composition, in step c) of obtaining the mixture of lactose, consists of physical mixing of lactoses with different particles sizes obtained according to normal mixing techniques. In a preferred embodiment of the invention, the lactoses used are Respitose® SV003 (DFE Pharma, Goch, D) and Lacto-Sphere® MM3 (Microsphere SA, Ponte Cremenaga, Lugano CH).

Step d) of the process for preparing the pharmaceutical composition instead consists of physical mixing of the powders obtained by spray drying and of the lactose mixture using the most common mixing techniques, i.e. rotating mixers such as Turbula, V-mixer, cylinder, double cone, cube mixers or stationary mixers used only for mixing, such as planetary, nautamix, sigma and ribbon mixers or mixer-granulators, such as Diosna. Besides these mixers, the powders could also be mixed with devices normally used to mix liquids, such as Ultra Turrax or Silverson and, ultimately, also inside fluid bed granulation devices. According to the present invention the pharmaceutical formulation for inhalation use comprising Budesonide and Formoterol is used mainly for the treatment of asthma (both in maintenance therapy and on an as-needed basis) and of chronic obstructive pulmonary disease. (COPD)

Due to the aerodynamic performance of the pharmaceutical composition for inhalation use according to the present invention, mostly because of the morphology of the powders and to their preparation process, which allows high deposition of this powder in the required site of action (lungs), it is possible to reduce the amount of active agent to be administered while still achieving an effective therapeutic activity based on the disease to be treated.

In particular, with a pharmaceutical composition for inhalation use according to the present description, it is possible to half the doses of active agent required to be administered, compared to the doses of active agent currently administered for the treatment of given diseases.

Reduction of the content the active agents is able, as a consequence, to reduce the side effects typical of administration of corticosteroids and of β2-agonists.

EXAMPLES

Methods for preparing the powders constituting the pharmaceutical composition of the present invention are described below.

Preparation of the Individual Powders.

The powders containing the active agents were obtained by spray drying, a drying technique used to obtain powders with uniform and amorphous particles from solutions of active agents and excipients in an appropriate solvent or mixture of solvents.

For the formulations described the solvents used were water and ethyl alcohol in a fixed ratio of 70/30. The concentration of dissolved solids was 1% p/v.

In the case of the powder containing Formoterol Fumarate as active agent, all the components of the powder were dissolved in water and the solution thus obtained was added to the portion of ethyl alcohol slowly at 25° C., taking care not to cause precipitation of some of the components.

In the formulation containing Budesonide as active agent, the active agent was dissolved separately in the alcohol portion to which the aqueous solution of the excipients was added to obtain a single water-alcohol solution.

The water-alcohol solution thus obtained was processed by means of a Buchi Mod. B290 spray dryer, using an open cycle with the following parameters:
nozzle diameter 0.7 mm
atomization gas nitrogen
atomization pressure 4 bar
drying gas air
aspiration 100% (35 m3/h)
inlet temperature 170° C.
feed speed 8% (2.4 ml/min)

Powder collection system: cyclone separator with glass collection vessel Outlet filter: polyester sleeve.

At the end of the drying process the powder collection step was performed in controlled temperature and humidity conditions: temperature <25° C., relative humidity <35%.

The powders were packaged immediately after production in borosilicate glass vials and inserted in a double aluminum foil bag heat-sealed under partial vacuum (30%).

Storage Conditions for Accelerated Stability Study.

The powders produced by spray drying, divided and packaged in borosilicate glass vials sealed inside in a double aluminum foil bag heat-sealed under partial vacuum (30%) were stored for an accelerated stability study in an oven at a temperature of 40° C. and relative humidity of 13%.

At each time interval established by the study, the samples corresponding to the stability point were taken, left to cool until reaching room temperature, opened in controlled conditions in a glove box (temperature<20° C., RH<35%) and analyzed as established in the protocol.

Characterization of the Powder: Particle Size Analysis.

The powders obtained, after spray drying, were characterized in terms of dry particle size using a Sympatec Helos light scattering device that analyzes the particle size according to the Fraunhofer theory and equipped with RODOS disperser.

The instrument was suitably calibrated with reference material and prepared following the instructions provided in the instrument user manual.

After appropriate cleaning before analysis, an amount of powder for each batch produced was analyzed without any preliminary preparation of the sample.

The dispersion gas used was compressed air suitably cleansed of particles.

The test method specified therefore provides for compliance with the following measures in relation to the sample, to the powder disperser and to the light scattering analyzer.

Sample
size: about 100 mg
feed procedure: with a spatula
pre-treatment of the sample: none
RODOS Disperser
Model M ID-NR 230 V/Hz 24Va
Dispersion pressure: 3 bar
Light Scattering Analyzer
Model: Helos
Test method: Fraunhofer
Software version: Windox 4.0
Test lens: R1 (0.1-35 μm)
Minimum optical concentration: 1%
Activation threshold: minimum detectable optical concentration 1% for a max time of 30 seconds and with sample exposure of at least 100 ms.

All the tests were conducted in controlled temperature and humidity environments, temperature<25° C. and relative humidity<50% RH.

Size analysis provides volume median diameter (VIVID) values of the population of particles in the sample of powder.

Characterization of the Powder: Residual Moisture Content.

The residual moisture content in the powder obtained by spray drying was measured using the Karl Fischer coloumetric system method.

The C20 Compact Karl Fischer Coulometer Mettler Toledo titrator was used for this purpose, which uses as reagent HYDRANAL®-Coulomat AG.

The sample powders were accurately weighed in an amount of around 15-20 mg and the weight was recorded in the parameters of the sample. Titration was started immediately after adding the sample to the reagent bath.

At the end of the test, the instrument indicates directly the percentage of water contained in the sample.

Characterization of the Powder: Determination of Titer and Related.

The HPLC (High Performance Liquid Chromatography) test method was used to determine the content of the active agents and their related substances.

The test method is characterized by the following parameters:

Solvent: 50/50 methanol/phosphate buffer pH 2.7 25 mM
Mobile phase: acetonitrile/phosphate buffer pH 2.9 2.82 mM gradient elution

| Time (min) | % ACN | % buffer pH 2.9 | Flow (ml/min) |
|---|---|---|---|
| 0 | 22 | 78 | 0.5 |
| 2.5 | 22 | 78 | 0.5 |
| 3.0 | 41 | 59 | 0.7 |
| 8.0 | 41 | 59 | 0.7 |
| 10.0 | 70 | 30 | 0.7 |
| 12.0 | 22 | 78 | 0.6 |
| 15.0 | 22 | 78 | 0.6 |

Injection volume: 20 μL
Analysis column: Agilent Poroshell 120 EC-C18, 100 mm×3.0 mm, 2.7 μm
Column temperature: 30
Wavelength: 220 nm (Formoterol Fumarate) and 240 nm (Budesonide)
Retention time: 2.4 min (Formoterol Fumarate) and 8.0 min (Budesonide)

An HPLC Agilent model 1200 with diode array type detector, model G1315C was used for the test.

The samples for analysis were obtained by dissolving in the solvent an amount of powder such as to obtain a concentration of 160 μg/ml for the Budesonide and 4.5 μg/ml for the Formoterol Fumarate, as for the reference solution.

The reference solution was injected three consecutive times before the sample to determine the precision of the system expressed as relative standard deviation percentage (RSD %), which must be less than 2%.

The active agent content is obtained by calculating the ratio of the areas with respect to the reference solution at known concentration. The degradation of the product is calculated as ratio between the sum of the areas of all the analysis peaks corresponding to the degradation products and the active agent taken as reference. The sum of the degradation products included all the analytical peaks with an area on the chromatogram greater than 0.1% of the area of the active agent.

Characterization of the Powder: Differential Scanning Calorimetry.

Differential scanning calorimetry or DSC is a thermoanalytical technique used to determine chemical and physical phenomena with endothermic or exothermic effect in a sample, such as variations in phase, loss of water and chemical reactions.

In DSC the sample is heated with constant heating speed and the amount of heat required to raise its temperature is a function of its thermal capacity. Each endothermic or exothermic phenomenon causes a reversible or irreversible change in the thermal capacity of the material and can be detected as a variation of the baseline of the thermogram.

Formulations containing amorphous lactose show during heating a typical decrease in thermal capacity corresponding to the glass transition of the lactose from amorphous solid state to a metastable state that rapidly leads to its crystallization, characterized by an exothermic peak.

The temperature corresponding to these phenomena varies as a function of the composition of the sample and of the environmental conditions in which the sample is stored and prepared.

The samples were prepared in a controlled environment (temperature<20° C., relative humidity 35-30%). 40 uL aluminum standard crucibles for DSC were filled with a weighed amount of powder between 1 mg and 3 mg and sealed with a specific lid. calorimetry testing of the samples in question was carried out by subjecting the samples to a heating ramp from 20 to 200° C. with a temperature increase of 10° C./min.

The test gives a thermogram in which the thermal events that accompany progressive heating of the sample are visible.

The glass transition (Tg) is identifiable with a decreasing step, at times followed by an increase in the baseline caused by relaxation enthalpy. During evaluation of the thermograms the onset temperature of the phenomenon (Tg onset) is calculated, regardless of the sample size. The glass transition temperature is a stability index of the powder as it is a prelude to crystallization, which takes place above 100° C. The exothermic crystallization peak can be integrated and the area subtended by the curve is an index of the amorphous fraction of the sample.

Preparation of the Mixtures.

The formulations used for the aerosol characterization test with MSLI, described in the examples, were produced by mixing powders containing the active agents and a powder containing the lactose mixture. Regardless of the quantitative ratios between initial powders, a layer-wise mixing technique was used, depositing the powder containing the active agent between two layers of lactose mixture, prepared in advance, in the mixing container. The powders were mixed using an Ultra Turrax T10 mixer for a mixing time of 5 minutes considered sufficient for the 3.5 g of powder of the batches produced. Uniformity of the content was controlled with titer analysis on 10 samples taken from different points of the bulk.

The powders were divided in sealed vials and stored inside a double aluminum foil bag heat sealed with partial vacuum (30%).

The operations of mixing and dividing in vials were carried out inside a glove box in controlled humidity and temperature conditions; max temperature 20° C. and environmental relative humidity <35%.

Characterization of the Powder: Respirability Test with MSLI.

The Multi Stage Liquid Impinger (MSLI) is a device that simulates in vitro pulmonary deposition of an inhalation formulation. A inhalation formulation, delivered by appropriate inhaler and conveyed into the device by aspiration, is deposited in the various stages connected in series of the impactor as a function of its aerodynamic features, such as particle size, density, shape. Each stage of the MSLI corresponds to an interval of aerodynamic particle sizes of the powder deposited therein. The aerodynamic size distribution of the powder is obtained using HPLC testing to determine the amount of active agent in each stage, making it possible to calculate the median aerodynamic diameter and the respirable fraction, considered according to the European Pharmacopoeia with aerodynamic diameter <5.0 μm.

For the respirability test, the powders of the formulations of the examples were divided into Size 3 HPMC capsules and loaded from RS01 powder inhaler—model 7 single-dose, code 239700001AB (Plastiape S.p.A., Osnago, Lecco, I).

The device was assembled following the instructions for use and the indications of the European Pharmacopoeia.

For test purposes, it is necessary to deliver 10 powder capsules for each respirability test. The tests were conducted at a flow of 96 lpm for 2.4 seconds deriving from a pressure drop of 4 KPa in the system.

The following aerodynamic diameter cut-offs correspond to this flow value for each stage.

stage 1: >10.3 μm stage 2: from 10.3 μm to 5.4 μm stage 3: from 5.4 μm to 2.5 μm stage 4: from 2.5 μm to 1.3 μm stage 5 (filter): <1.3 μm The respirable fraction (Fine Particle Fraction) comprises particles having a median aerodynamic diameter of less than 5.0 μm and is calculated using specific software (CITDAS Copley).

The aerodynamic parameters of an inhalation formulation subjected to MSLI analysis are expressed in terms of:

- Delivered Fraction (DF): i.e. the percentage of the dose of active agent delivered from the mouthpiece of the inhaler
- Fine Particle Fraction (FPF): respirable fraction (aerodynamic diameter<5.0 μm) of active agent expressed as percentage of the amount delivered. Quantitative determination of the active agent in each stage was performed by HPLC using the test method for titer and related.

Example 1

Example 1 was conducted producing formulations containing Formoterol Fumarate, which is an active agent sensitive to the presence of free water in the formulation.

Together with formoterol, formulations containing different amounts of leucine and lactose or mannitol were produced.

The example highlights the protective effect of lactose against formoterol; this protective effect is explained considering that lactose is capable of producing a scavenger effect against the free water present in the formulation.

To demonstrate this, formulations of 3 types were produced:

- A powder containing exclusively formoterol and leucine
- 2 powders with different lactose contents together with lactose and leucine
- 2 powders in which lactose was substituted by a different sugar: mannitol The formulations with lactose tend to acquire moisture over time, with consequent decrease of Tg, but degradation over time is limited. This limited degradation is presumably due to a scavenger effect produced by the lactose against the water, which is thus trapped in a rigid structure and prevented from reacting with the other components. Differently, the formulation without lactose which was already crystalline undergoes chemical degradation.

Of the two formulations containing lactose, the one with 50% is better, as it is more stable over time.

TABLE 1A

| Ex. | Active | Formoterol (%) | Leucine % | Sugar | Water content (%) T0 | Water content (%) T28 (days) |
|---|---|---|---|---|---|---|
| 1 | Formoterol | 5 | 95 | NO Sugar | 0.9 | 0.9 |
| 2 | Formoterol | 5 | 70 | Lactose | 1.4 | 1.8 |
| 3 | Formoterol | 5 | 45 | Lactose | 2.1 | 2.7 |
| 4 | Formoterol | 5 | 70 | Mannitol | 0.9 | 0.9 |
| 5 | Formoterol | 5 | 45 | Mannitol | 1 | 0.9 |

TABLE 1B

| Ex. | Tg (° C.) T0 | Tg (° C.) T28 days | P.size (μm) T0 | P.size (μm) T28 days | Degradation (%) T0 | Degradation (%) T28 days |
|---|---|---|---|---|---|---|
| 1 | Not detected | Not detected | 2.6 | 2.7 | 0.6 | 0.9 |
| 2 | 62.7 | 56.9 | 2 | 1.9 | 0.4 | 0.4 |
| 3 | 66.3 | 57.5 | 1.6 | 1.6 | 0.3 | 0.3 |
| 4 | Not detected | Not detected | 2.3 | 2.2 | 0.2 | 1.6 |
| 5 | Not detected | Not detected | 1.6 | 1.6 | 0.1 | 1.4 |

Example 2

The example was conducted producing formulations containing as active agent Budesonide, defined as HLSA Bud, formulated with lactose and leucine (Table 3), formulations containing as active agent Formoterol Fumarate, defined as HLSA FF, formulated with lactose and leucine (Table 2).

The lactose powders used were Respitose SV003 and LactoSphere MM3. Identification of the optimal coarse/fine lactose ratio was based on the production of formulations with increasing amounts of LactoSphere MM3 in formulations containing HLSA FF, HLSA Bud and Respitose SV003 due to the aerodynamic characterization of each single formulation. The parameters evaluated through the MSLI test were the Fine Particle Fraction (FPF %) and the Delivered Fraction (DF %) in conditions with pressure drop of 4 KPa using the inhaler RS01 (Plastiape, Osnago, Lecco, I).

The results obtained show that a ratio of 91:9 Respitose SV003 (coarse lactose) and MM3 (fine lactose) guarantees high values of Delivered Fraction (%) and high Fine Particle Fraction (%) respirability, at the same time ensuring that the mixture remains homogeneous over time.

TABLE 2

Powder containing Formoterol Fumarate (HLSA FF 2.25%)

| | |
|---|---|
| Formoterol Fumarate | 2.25% |
| Leucine | 20.0% |
| Lactose | 77.25% |
| Tween 80 | 0.5% |

TABLE 3

Powder containing Budesonide (HLSA Bud 8%)

| | |
|---|---|
| Budesonide | 8.0% |
| Leucine | 50.0% |
| Lactose | 41.5% |
| Tween 80 | 0.5% |

TABLE 4

Powder containing Lactose Mix

| Ex. | Respitose SV003 | Lactosphere MM3 |
|---|---|---|
| 6 | 100.0% | 0.0% |
| 7 | 98.0% | 2.0% |
| 8 | 94.0% | 6.0% |
| 9 | 91.0% | 9.0% |
| 10 | 90.0% | 10.0% |
| 11 | 85.0% | 15.0% |
| 12 | 80.0% | 20.0% |
| 13 | 70.0% | 30.0% |

TABLE 5

| Ex. | HLSA FF | HLSABDS | Lactose mix from Table 4 |
|---|---|---|---|
| 14 | 0.5% | 2.5% | From example 6 97% |
| 15 | 0.5% | 2.5% | From example 7 97% |
| 16 | 0.5% | 2.5% | From example 8 97% |
| 17 | 0.5% | 2.5% | From example 9 97% |
| 18 | 0.5% | 2.5% | From example 10 97% |
| 19 | 0.5% | 2.5% | From example 11 97% |
| 20 | 0.5% | 2.5% | From example 12 97% |
| 21 | 0.5% | 2.5% | From example 13 97% |

TABLE 6

| Ex. | DF % MSLI Formoterol | DF % MSLI Budesonide | FPF % MSLI Formoterol | FPF % MSLI Budesonide |
|---|---|---|---|---|
| 14 | 81.4% | 85.3% | 59.8% | 51.5% |
| 15 | 81.3% | 87.0% | 59.7% | 49.1% |
| 16 | 86.3% | 91.3% | 69.2% | 68.7% |
| 17 | 88.3% | 90.6% | 67.6% | 69.6% |
| 18 | 89.2% | 92.8% | 65.6% | 63.8% |
| 19 | 95.5% | 97.4% | 63.0% | 66.5% |
| 20 | 80.8% | 79.6% | 53.9% | 66.8% |
| 21 | 80.6% | 80.5% | 48.2% | 63.1% |

Example 3

Example 3 was conducted producing formulations containing as active agent Budesonide (defined as HLSA Bud in the table), formulated with lactose and leucine, and formulations containing as active agent Formoterol Fumarate (defined as HLSA FF in the table), formulated with lactose and leucine. These formulations were mixed with a lactose powder containing a mixture of Repitose SV003 and of LactoSphere MM3. The powders contained in the composition according to the invention are as follows:

TABLE 7A

Powder containing Formoterol Fumarate (HLSA FF)

| | |
|---|---|
| Formoterol Fumarate | 2.25% |
| Leucine | 20.0% |
| Lactose | 77.25% |
| Tween 80 | 0.5% |

TABLE 7B

Powder containing Budesonide (HLSA Bud)

| | |
|---|---|
| Budesonide | 8.0% |
| Leucine | 50.0% |
| Lactose | 41.5% |
| Tween 80 | 0.5% |

TABLE 7C

Lactose Mix

| | |
|---|---|
| Repitose SV003 and LactoSphere MM3 | 91% 9% |

The three powders were mixed according to methods described above, in order to obtain three formulations containing Budesonide and Formoterol in a dose of powder of 15 mg. The three formulations obtained contain an amount of active agent referable to three compositions available on the market, precisely the amount of powders is half the amount normally administered.

The aerodynamic performance of the three formulations prepared as described above was assessed with the MSLI test at the pressure drop of 4 KPa with the inhaler RS01.

The DUSA test as described was also conducted at the same time.

TABLE 8

Composition of Formulations at 15 mg (Budesonide/Formoterol μg)

| | A1 (160/4.5) | A2 (80/2.25) | A3 (40/2.25) |
|---|---|---|---|
| HLSA FF | 1.6% | 0.8% | 0.8% |
| HLSA Bud | 16% | 8% | 4% |
| Lactose mix | 82.4% | 91.2% | 95.2% |

TABLE 9

| Ex. | DF % DUSA Formoterol | DF % DUSA Budesonide | FPF % MSLI Formoterol | FPF % MSLI Budesonide |
|---|---|---|---|---|
| A1 | 87.1 | 89.2 | 72.2 | 73.7 |
| A2 | 81.5 | 84.9 | 74.2 | 75.3 |
| A3 | 85.6 | 87.3 | 66.6 | 67.3 |

Example 4

The example was conducted analyzing the products currently on the market at different formulations (Table 10) and analyzing crystalline mixtures of budesonide and formoterol (i.e. not formulated according to the present invention by spray drying) with lactose mixtures with different particle sizes according to the present invention (Tables 11 and 12).

The product available on the market used for comparison was Symbicort®, produced by Astrazeneca, which is present in three different compositions with a Budesonide/Formoterol Fumarate ratio expressed in μg of 320/9, 160/4.5 and 80/4.5.

The example was conducted in order to assess the aerosol performance of the composition according to the present invention, emphasizing how this composition (see Example 3) can be administered at half the dose of the aforesaid formulation of reference currently on the market.

The reduction of the administered dose takes place:— while maintaining a high dose of drug delivered through the mouthpiece and a percentage of fine particles able to ensure that the amount of drug deposited in the site of action is capable of performing the correct pharmacological action;— at the same time reducing the characteristic side effects of the administered drugs.

The aerodynamic performance of the three formulations prepared as described above was assessed with the MSLI test conducted at 4 KPa.

TABLE 10

| | FPF % MSLI Formoterol | FPF % MSLI Budesonide |
|---|---|---|
| Symbicort 320/9 | 60.2 | 57.2 |
| Symbicort 160/4.5 | 52.7 | 54.8 |
| Symbicort 80/4.5 | 60.4 | 61.4 |

TABLE 11

Crystalline Budesonide and Formoterol powder C1

| | |
|---|---|
| Budesonide Micronized Ph.Eur., Industriale Chimica, S.r.I, Saronno, VA, Italy | 0.64% |
| Formoterol Fumarate Dihydrate, Ph Eur. 7th Ed., Lusochimica, S.p.A., Lomagna, LC, Italy | 0.018% |
| Lactose Mix (according to Table 2C) | 99.342% |

TABLE 12

| Ex. | DF % DUSA Formoterol | DF % DUSA Budesonide | FPF % MSLI Formoterol | FPF % MSLI Budesonide |
|---|---|---|---|---|
| C1 | 70.4% | 65.7% | 3.7% | 46.6% |

The invention claimed is:

1. A pharmaceutical composition for inhalatory use in the form of powder, is obtained by preparing:
    a) a first powder comprising budesonide or a pharmaceutically acceptable salt thereof, in an amount greater than 5% by weight of said first powder, leucine in an amount from 5 to 70% by weight of said first powder, lactose in an amount from 20 to 90% by weight of said first powder;
    b) a second powder comprising formoterol or a pharmaceutically acceptable salt thereof, in an amount greater than 1% by weight of said second powder, leucine in an amount from 5 to 70% by weight of said second powder, lactose in an amount from 20 to 90% by weight of said second powder; and
    c) a third powder comprising a mixture of a first lactose which has an X50 from 35 to 75 μm, with a second lactose which has an X50 from 1.5 to 10 μm, the content of said first and second lactose in said mixture being respectively from 85% to 96% and from 4% to 15%; and
    d) blending said first powder, said second powder and said third powder to form a single mixture;
    wherein the ratio by weight of the total of said first and second powder and mixture of a first and second lactose is from 1/5 to 1/100, and said composition has a fine particle fraction (FPF) greater than 60% and a delivered fraction (DF) greater than 80%.

2. The composition according to claim 1, wherein said first and said second powder comprise a surfactant in an amount from 0.2 to 2% by weight of each powder.

3. The composition according to claim 1, wherein said leucine is present in said first and second powder in an amount from 18 to 55% by weight.

4. The composition according to claim 1, wherein said lactose is present in said first and second powder in an amount from 40 to 80% by weight.

5. The composition according to claim 2, wherein said surfactant is selected from the group consisting of benzalkonium chloride, cetrimide, docusate sodium, glyceryl monooleate, sorbitan esters, sodium lauryl sulfate, polysorbates, phospholipids, biliary salts, polysorbates, block copolymers of polyoxyethylene and polyoxypropylene.

6. The composition according to claim 2, wherein said surfactant is present in an amount from 0.4 to 0.8% by weight.

7. The composition according to claim 1, wherein said first and second powder have an X50 of less than 5 μm.

8. The composition according to claim 1, wherein the budesonide is in an amount from 30 to 200 μg and the formoterol is in an amount from 1.5 to 6 μg per inhalatory unit dose.

9. A kit for the administration of a drug as inhalatory powder, comprising a metered amount of the composition according to claim 1 and a device for inhalation.

10. The composition according to claim 2, wherein said leucine is present in said first and second powder in an amount from 18 to 55% by weight.

11. The composition according to claim 2, wherein said lactose is present in said first and second powder in an amount from 40 to 80% by weight.

12. The composition according to claim 3, wherein said surfactant is selected from the group consisting of benzalkonium chloride, cetrimide, docusate sodium, glyceryl monooleate, sorbitan esters, sodium lauryl sulfate, polysorbates, phospholipids, biliary salts, polysorbates, block copolymers of polyoxyethylene and polyoxypropylene.

13. The composition according to claim 4, wherein said surfactant is selected from the group consisting of benzalkonium chloride, cetrimide, docusate sodium, glyceryl monooleate, sorbitan esters, sodium lauryl sulfate, polysorbates, phospholipids, biliary salts, polysorbates, block copolymers of polyoxyethylene and polyoxypropylene.

14. The composition according to claim 3, wherein said surfactant is present in an amount from 0.4 to 0.8% by weight.

15. The composition according to claim 4, wherein said surfactant is present in an amount from 0.4 to 0.8% by weight.

16. The composition according to claim 5, wherein said surfactant is present in an amount from 0.4 to 0.8% by weight.

17. The composition according to claim 1, wherein said first and second powder have an X50 of less than 3 μm.

18. The composition according to claim 2, wherein said first and second powder have an X50 of less than 5 μm.

19. The composition according to claim 3, wherein said first and second powder have an X50 of less than 5 μm.

20. The composition according to claim 4, wherein said first and second powder have an X50 of less than 5 μm.

* * * * *